United States Patent [19]

Sederholm et al.

[11] Patent Number: 5,643,271
[45] Date of Patent: Jul. 1, 1997

[54] ANGLED ORTHOPEDIC SURFACER AND GUIDE

[75] Inventors: Gary W. Sederholm, Austin, Tex.; Kenneth A. Gustke, Tampa, Fla.; Janet L. Krevolin, Austin, Tex.

[73] Assignee: Sulzer Orthopedics Inc., Austin, Tex.

[21] Appl. No.: 303,628

[22] Filed: Sep. 9, 1994

[51] Int. Cl.$^6$ .................................................. A61B 17/56
[52] U.S. Cl. .................................. 606/80; 606/79; 606/87
[58] Field of Search ................................ 606/96, 89, 97, 606/98, 80, 81, 84, 85, 79, 86, 99, 102; 408/3, 115 B, 72 B, 127, 202, 203, 241 G; 81/177.7, 177.75

[56] References Cited

U.S. PATENT DOCUMENTS

| | | | |
|---|---|---|---|
| 2,181,746 | 11/1939 | Siebrandt | 606/96 X |
| 4,710,075 | 12/1987 | Davison | 408/202 |
| 4,722,331 | 2/1988 | Fox | 606/96 X |
| 4,860,735 | 8/1989 | Davey et al. | 606/96 X |
| 5,112,336 | 5/1992 | Krevolin et al. | 606/96 |
| 5,152,744 | 10/1992 | Krause et al. | 604/22 |
| 5,236,289 | 8/1993 | Sayler | 408/127 |
| 5,344,423 | 9/1994 | Dietz et al. | 606/87 |
| 5,403,320 | 4/1995 | Luman et al. | 606/89 |

FOREIGN PATENT DOCUMENTS 2722334   12/1977   Germany .............................. 606/180

*Primary Examiner*—Guy V. Tucker
*Attorney, Agent, or Firm*—Richard L. Robinson

[57] ABSTRACT

An angled orthopedic surfacer and guide which is particularly useful in connection with revision surgeries for femoral hip prostheses. The surfacer comprises a drive shaft connected to a milling head through a U-joint. A housing for the U-joint supports an adjustable spacer which can be moved to selected positions to control the depth of cut. A pivoting guide connects the surfacer to a rasp used to ream out a cavity for a prosthesis. The surfacer can be pivoted around a proximal and medial side of the rasp to cut away bone.

11 Claims, 4 Drawing Sheets

ANGLED ORTHOPEDIC SURFACER AND GUIDE

BACKGROUND OF OUR INVENTION

Our invention relates to apparatus for preparing human bone to receive an implanted prosthesis, and particularly to receive a femoral hip prosthesis.

Various types of femoral hip prostheses are known and are used for surgical reconstruction of the hip joint. In general, these prostheses comprise a ball-shaped head mounted at an anatomical angle on a stem. The stem can be thrust into the medullar canal of the femur to mount the prosthesis at a resected surface of the femur. Many of these prostheses have collars near their proximal end which rest upon the resected surface. Both permanently attached collars and replaceable collars are known. In some cases, however, a patient's femur may have insufficient bone mass near the proximal end of the femur to support the collar or, during revision surgery when a second operation is necessary, additional bone may be removed. To restore a prosthesis to an anatomically correct position, the prosthesis would protrude further out of the remaining femur, leaving a gap between the collar and the resected surface of the femur. Spacers or other apparatus have been proposed to fill this gap. Such a femoral hip prothesis with spacer is described in U.S. patent application 08/101,421, filed Aug. 3, 1993, an application assigned to Intermedics Orthopedics, Inc.

We have found that it is important to accurately prepare the proximal surface of the femur to receive such a femoral hip prosthesis. In particular, it is sometimes necessary to mill away a portion of the femur medially and proximally on the femur, below an area which is normally covered by a collar. This area is difficult to reach during the revision operation.

SUMMARY OF OUR INVENTION

We have invented an angled orthopedic surfacer and guide which is particularly useful in connection with revision surgeries for femoral hip prostheses. The surfacer comprises a drive shaft connected to a milling head through a U-joint. A housing for the U-joint supports an adjustable spacer which can be moved to selected positions to control the depth of cut. A pivoting guide connects the surfacer to a rasp used to ream out a cavity for a prosthesis. The surfacer can then be pivoted around a proximal and medial side of the rasp to cut away diseased or weakened bone, thus preparing a suitably strong and healthy surface for a revision prosthesis and spacer.

It is an object of our invention, therefore, to provide an apparatus for milling a proximal medial area on a femur during revision surgery.

It is further an object of our invention to provide an apparatus which provides an angled drive mechanism to adapt for use in confined conditions during revision surgery.

Another object of our invention is to provide an apparatus which can accurately provide a revision collar surface at selected depths.

A further object of our invention is to provide an apparatus for surgical use with an angled drive mechanism.

These and other advantages and objects of our invention will be apparent to those skilled in the art from the following detailed description taken with reference to the accompanying drawings.

DETAILED DESCRIPTION OF OUR PREFERRED EMBODIMENT

In referring to the accompanying drawings, like numerals will refer to like parts throughout this description.

Figure 1:
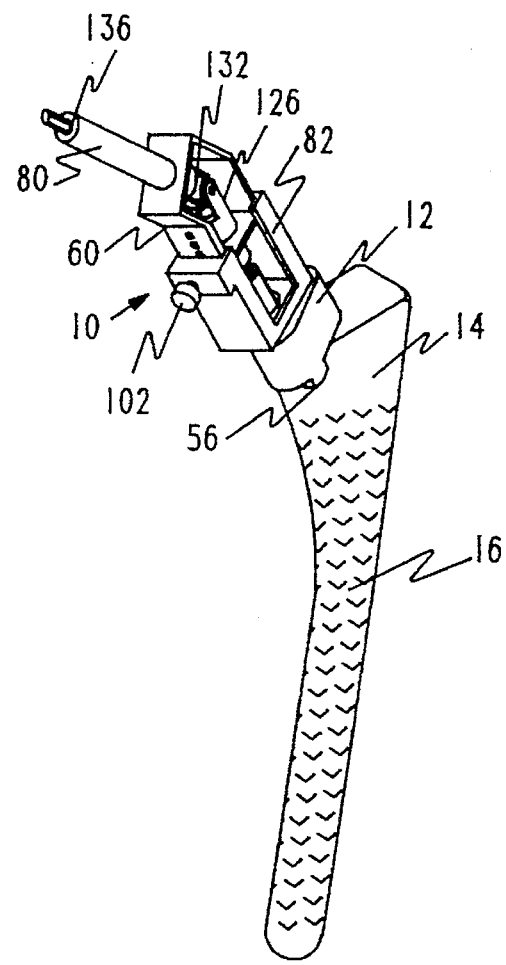
FIG. 1 is a perspective view of an orthopedic surfacer and guide according to our invention, mounted on a surgical rasp.

In FIG. 1, a perspective view of the angled orthopedic surfacer, generally designed 10, is shown mounted on a pivoting guide 12. The guide 12 pivots on a proximal end 14 of a surgical rasp 16. Surgical rasps are well-known in the art and need not be described in detail here. They are utilized to ream out an appropriate cavity in a medullar canal of a patient for receiving a hip prosthesis, such as hip prosthesis 18 illustrated in FIG. 2.

Figure 2:
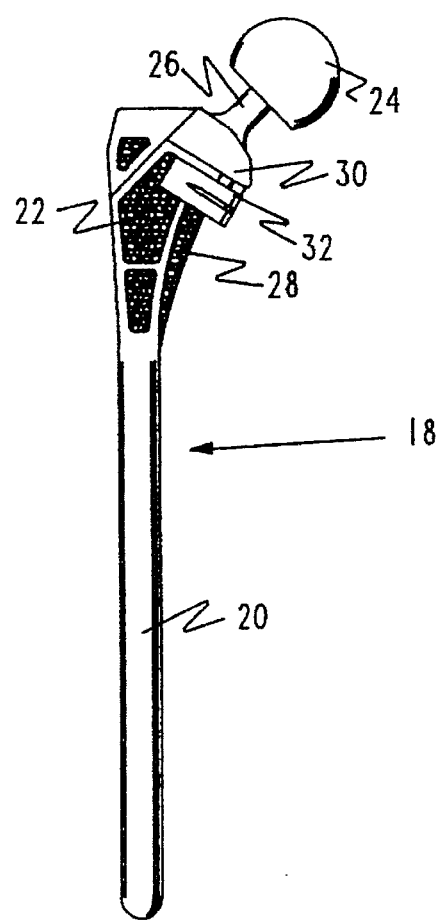
FIG. 2 is a plan view of a femoral prosthesis with spacer.

The orthopedic surfacer of our invention finds particular application in connection with revision hip prostheses, of which the hip prosthesis 18 is an example. A revision prosthesis is implanted after a first or primary prosthesis has failed. As seen in FIG. 2, such a prosthesis may comprise an elongated stem 20, an enlarged proximal portion 22, and a head 24. The head 24 is connected to the proximal portion 22 by a neck 26. Frequently, the proximal portion 22 has fixation features of some kind, for example porous areas 28. A collar 30 is frequently a feature of such prostheses. Collars act against a proximal resected surface on a femur to prevent the prosthesis from sinking into the medullar canal. However, in revision surgeries particularly, it may occur that the proximal portion of the bone is substantially weakened. In order to reach bone of sufficient strength, some of the proximal and medial portion of the femur may be removed and a spacer 32 inserted under the collar.

To prepare the bone to receive the prosthesis 18, the medullar canal of the femur may be drilled in a known manner and then the rasp 16 may be driven into the cavity, further shaping the medullar canal. When the rasp 16 has been driven into the femur to the appropriate position, the orthopedic surfacer 10 of our invention may be employed. The rasp 16 frequently has a proximal post or pin (not shown) at the proximal end 14 of the rasp. The guide 12 can be pivotally mounted on this post. The orthopedic surfacer 10 can then be inserted in the guide to a selected depth. The assembled apparatus is then pivoted around the post on the rasp 16 to mill away a proximal and medial portion of the femoral bone, preparing a site for the spacer. We will now describe the guide 12 and surfacer 10 in greater detail.

Figure 6:
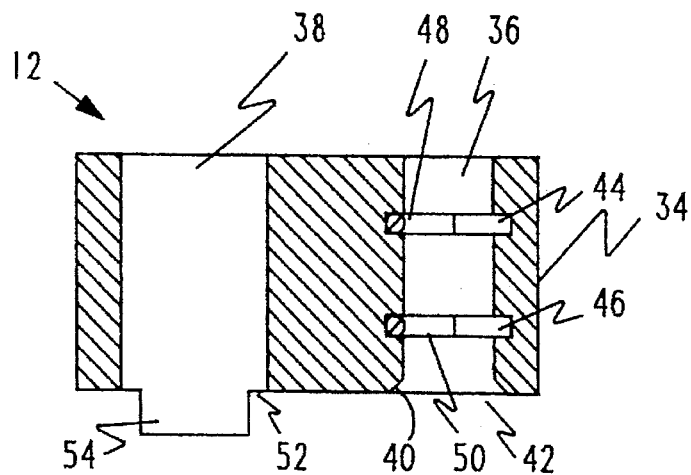
FIG. 6 is a through section of the guide of FIG. 5 taken along line 6—6.
Figure 5:
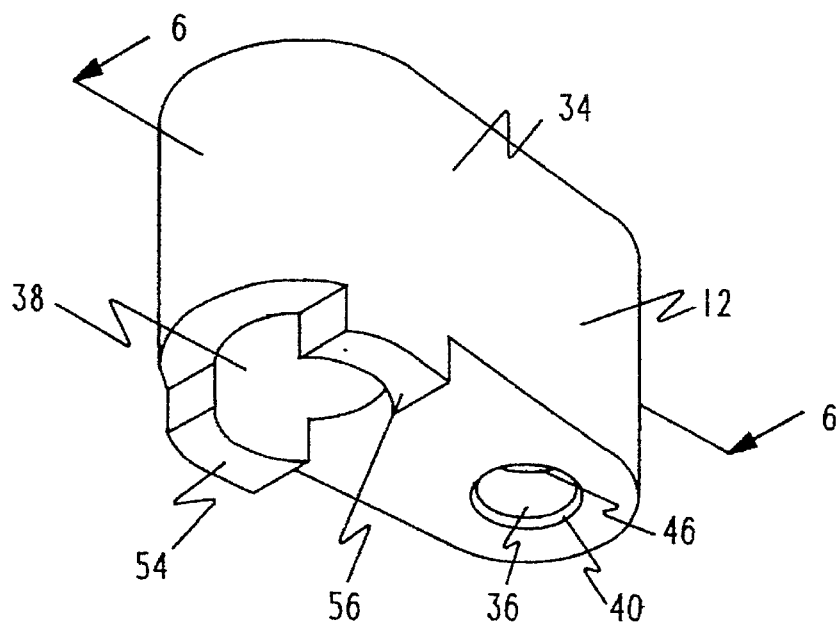
FIG. 5 is a perspective view of a pivoting guide for use with the surfacer.

The guide 12 is illustrated in FIGS. 5 and 6. The guide 12 comprises a body 34 having a rasp post bore 36 and cutter bore 38 at opposites ends of the body. The bores 36, 38 are spaced apart from one another but are substantially parallel to one another. The rasp post bore 36 is sized to receive the post or pin on the rasp 16. A chamfer 40 is provided at a distal end 42 of the post bore 36 to facilitate assembly. Two parallel grooves 44, 46 are provided circumferentially within the post bore 36. These grooves 44, 46 house split ring guide wires 48, 50 which provide a stable connection with the pin on the rasp 16. In our preferred embodiment, these guide wires are round in cross section, and relatively open, circumscribing about 240° of circumference.

The cutter bore 38 can be accurately sized to match its orthopedic surfacer 10. At a distal end 52 of the cutter bore 38 are two stops 54, 56. These stops, 54, 56 shield the rasp 16 and prevent the orthopedic surfacer 10 from milling into the rasp as the apparatus is pivoted around the post.

Figure 3:
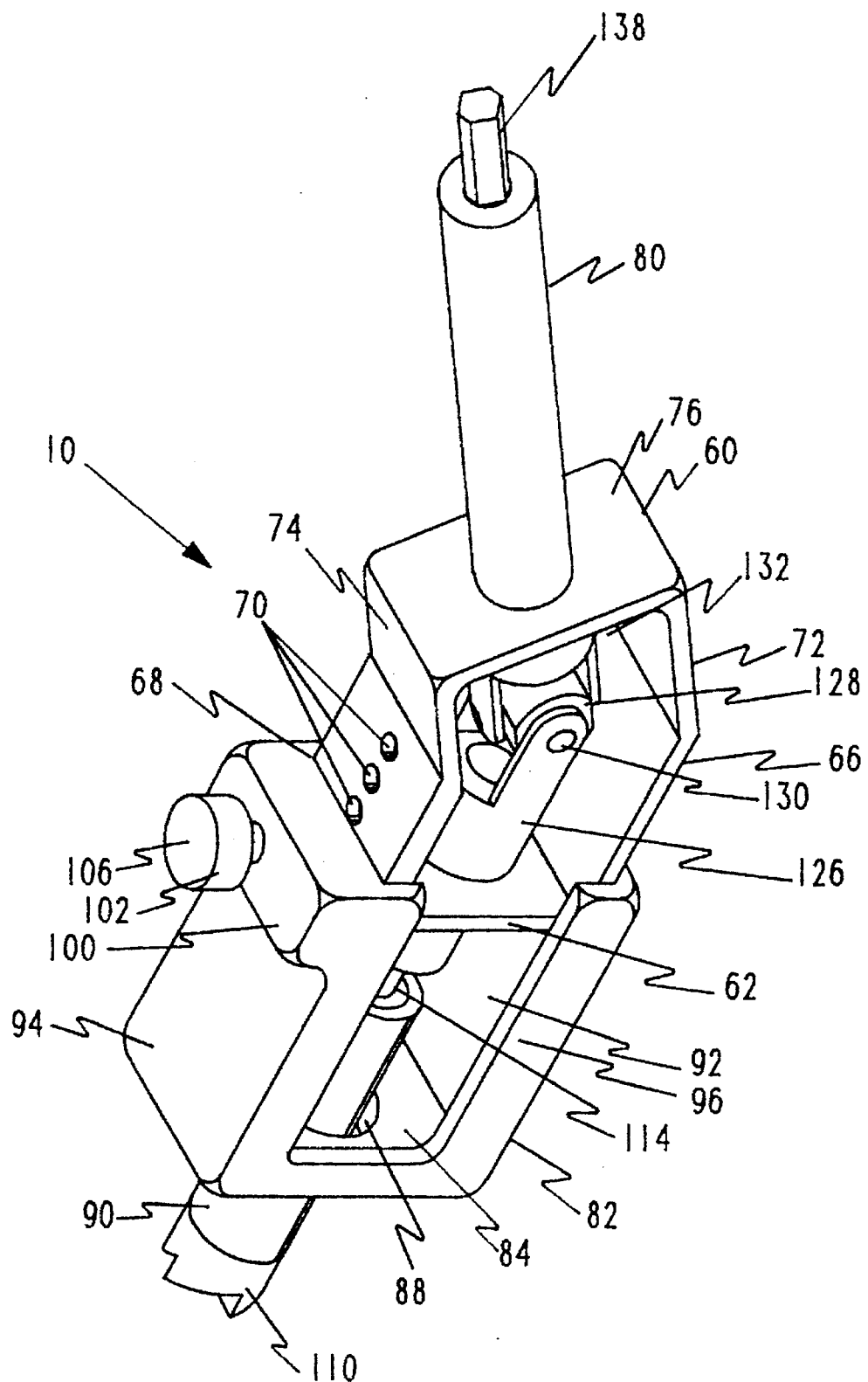
FIG. 3 is a perspective view of the orthopedic surfacer according to our invention.
Figure 4:
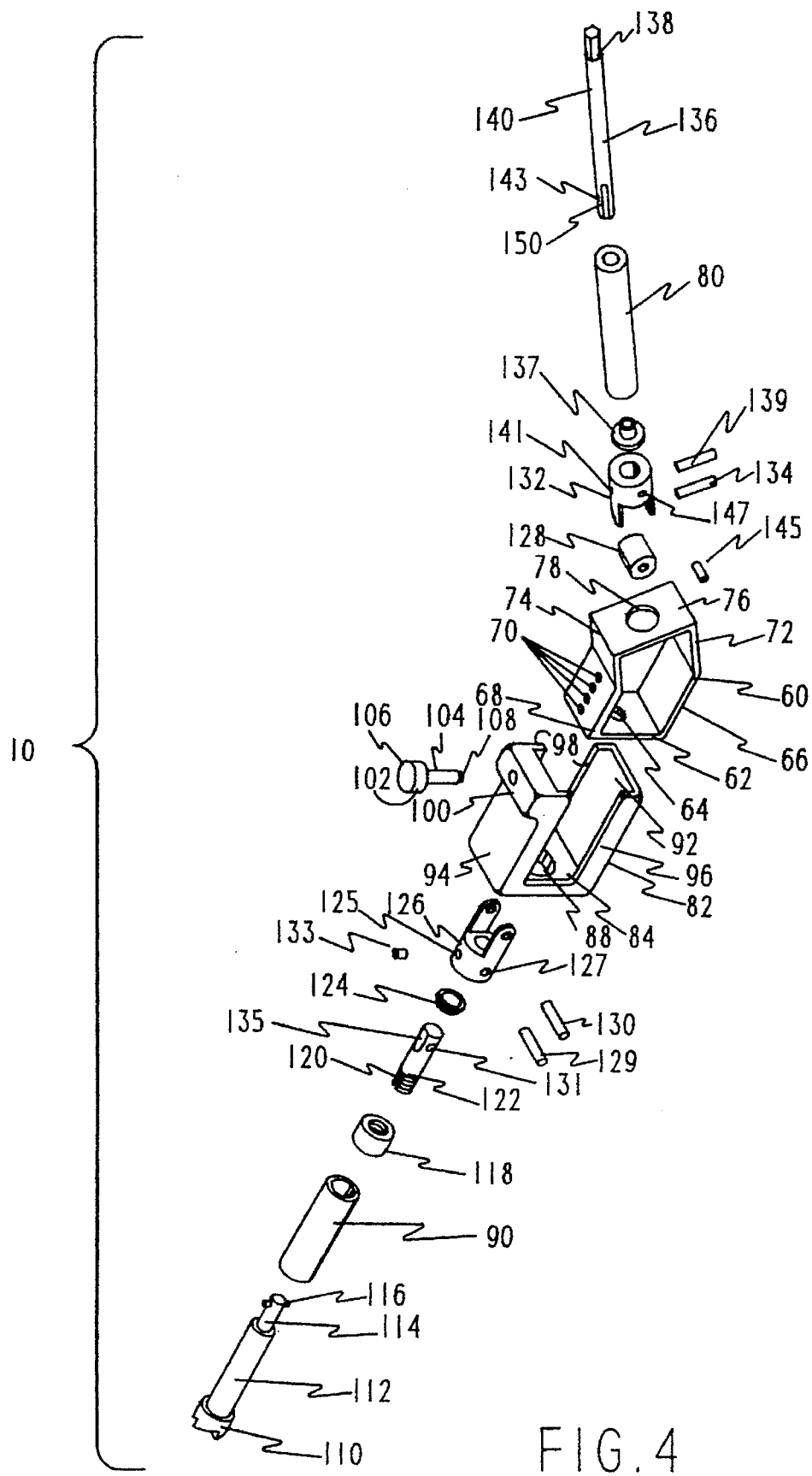
FIG. 4 is an exploded perspective view of the surfacer of FIG. 3.

The orthopedic surfacer 10 is shown assembled in perspective view in FIG. 3 and in exploded view in FIG. 4. The surfacer 10 comprises a housing 60. The housing 60 is angled such that in outline it appears as the intersection of two rectangles. Only walls are provided: the top and bottom are open so that the surfacer can be sterilized. More particularly described, the housing 60 comprises a distal wall 62 with a central bore 64. Two parallel walls 66, 68 join the distal wall 62. In one of the walls, for example wall 68, a series of holes 70 are provided for use with a spacer, to be described hereafter. Two mutually parallel angled walls 72, 74 join the parallel walls 66, 68. The angled walls 72, 74 are connected by a proximal end wall 76 which also has a central bore 78 therein. A sleeve 80 is attached to the proximal wall 76 over the central bore 78 in a suitable manner, for example by welding.

An adjustable spacer 82 fits over the parallel walls 66, 68 adjacent the distal wall 62. The adjustable spacer 82 is generally a channel iron formed into a U-shape. It comprises a distal wall 84 which confronts the distal wall 62 of the housing 60. A central bore 88 is also provided in this wall 84. The adjustable spacer 82 also has two parallel walls 92, 94 which slidingly engage the parallel walls 66, 68 of the housing 60. Rims 96, 98 are connected along the parallel walls 92, 94 and the distal wall 84. These rims 96, 98 guide the adjustable spacer along the housing 60. A threaded receptacle 100 is attached to one of the walls, for example wall 94 of the spacer 82 and receives a plunger 102. The plunger 102 has a threaded shaft 104 and a knob 106. A pin 108 opposite the knob 106 can be inserted into a selected one of the holes 70 on the housing 60 to control the placement of the adjustable spacer 82 with respect to the housing 60.

The cutting action of the surfacer 10 is accomplished by a milling head 110 on a shaft 112. The shaft 112 rides in a protective sleeve 90. The shaft 112 has a proximal end 114 of reduced cross section with a transverse pin 116 for removably connecting the milling head to the surfacer 10. This is accomplished by passing the proximal end 114 through a threaded nut 118 and into a slot 120 in a threaded rod 122. The nut 118 is then tightened onto the rod 122 to clamp the pin 116 within the slot 120. The rod 122 passes through a bushing 124 which rides in the bore 64 in the housing 60. The rod 122 is attached to a first U-connector 126 by a pin 129 inserted in a cross bore 127 in the U-connector 126 and in a cross bore 131 in the rod 122. Additional torsional strength may be provided by using a set screw 133 screwed into a threaded bore 125 in the U-connector 126. The set screw 133 presses against a flat 135 on the rod 122.

The first U-connector is pivotally attached to a pivot 128 with a U-joint pin 130. At 90° to the first U-connector 126, a second U-connector 132 is also pivotally connected to the pivot 128 by a second U-joint pin 134. The two U-connectors 126, 132, the pivot 128 and the associated pins 130, 134 comprise a U-joint which rides within the angled housing 60, as can best be seen in FIG. 3. The U-joint is driven by a drive shaft 136 which passes through the sleeve 80 and a bushing 137 and into the second U-connector 132. The drive shaft 136 is connected to the second U-connector 132 by a pin 139 inserted in a cross bore 141 in the U-connector 132 and in a cross bore 143 in the drive shaft 136. As with the rod 122, additional torsional strength may be provided by using a set screw 145 screwed into a threaded bore 147 in the U-connector 132. The set screw 145 presses against a flat 150 on the drive shaft 136.

The drive shaft 136 has a connector 138 at a proximal end 140 thereof. The connector is of any type suitable for connection to a source of rotary power, such as are commonly available for surgical applications and are well-known in the art.

In use, the depth of cut of the milling head 110 can be set by manipulating the adjustable spacer 82 along the housing 60. The provision of a U-joint and angled power drive permits the use of this apparatus in the confined conditions available during surgery.

Our invention may be embodied in other specific forms without departing from the spirit or essential characteristics thereof. The present embodiment is therefore considered in all aspects as illustrative and not restrictive, the scope of our invention being indicated by the appended claims rather than the foregoing description, and all changes which come within the meaning and range of equivalency of the claims are therefore intended to be embraced therein.

We claim as our invention:

1. An orthopedic apparatus comprising means for cutting bone, means for receiving torsional forces, said receiving means having a first axis of rotation, means for turning said means for cutting bone, said turning means having a second axis of rotation, said second axis being non-parallel with respect to said first axis, a U-joint for translating said torsional forces from said receiving means to said turning means, a housing surrounding said U-joint, a spacer for selectively adjusting a depth of cut of said means for cutting bone, said spacer being slidingly received over said housing, and means for securing said spacer at a selected position with respect to said means for cutting bone.

2. The orthopedic apparatus according to claim 1 wherein said means for securing said spacer comprise a plunger and a plurality of holes in said housing for selectively receiving said plunger.

3. The orthopedic apparatus according to claim 2 wherein said means for cutting bone comprise a milling head.

4. The orthopedic apparatus according to claim 2 wherein said means for receiving torsional forces comprise a drive shaft and wherein said means for turning comprise a rod connected at one end to said U-joint and at a second end to said means for cutting bone.

5. The orthopedic apparatus according to claim 4 wherein said means for cutting bone comprise a milling head.

6. An orthopedic apparatus for surfacing a human bone, said apparatus comprising means for milling a selected portion of bone, said means for milling having
      a milling head,
      means for driving said milling head, and
      means for selectively adjusting a depth of cut of said milling head having a spacer slidingly received over at least a portion of said means for driving said milling head and means for securing said spacer means at a selected position with respect to said milling head, guide means for guiding said means for milling in an arcuate path around a selected axis relative to said human bone by pivoting said guide means about said axis, said selected axis being spaced away from said milling head, said guide means having at least two tabs on opposite sides of said guide means for limiting the pivoting of said guide means around said axis, and means for securing said guide means with respect to said human bone at said selected axis for pivoting said guide means around said selected axis, said means for driving said milling head comprising means for receiving torsional forces, said receiving means having a first axis of rotation, means for turning said milling head, said turning means having a second axis of rotation, said second axis being non-parallel with respect to said first axis, a U-joint for translating said torsional forces from said receiving means to said turning means, a housing surrounding said U-joint, and a spacer slidingly received over said housing and means for securing said spacer means at a selected position with respect to said milling head for selectively adjusting a depth of cut of said milling head.

7. The orthopedic apparatus according to claim 6 wherein said means for securing said spacer comprise a plunger and a plurality of holes in said housing for selectively receiving said plunger.

8. The orthopedic apparatus according to claim 7 wherein said means for receiving torsional forces comprise a drive shaft and wherein said means for turning comprise a rod connected at one end to said U-joint and at a second end to said milling head.

9. An orthopedic apparatus for surfacing a human bone, said apparatus comprising means for milling a selected portion of bone, said means for milling having a milling head and means for driving said milling head, guide means for guiding said means for milling in an arcuate path around a selected axis relative to said human bone by pivoting said guide means about said axis, said selected axis being spaced away from said milling head, and means for securing said guide means with respect to said human bone at said selected axis for pivoting said guide means around said selected axis, said means for driving said milling head comprising means for receiving torsional forces, said receiving means having a first axis of rotation, means for turning said milling head, said turning means having a second axis of rotation, said second axis being non-parallel with respect to said first axis, a U-joint for translating said torsional forces from said receiving means to said turning means, a housing surrounding said U-joint, and a spacer slidingly received over said housing and means for securing said spacer means at a selected position with respect to said milling head for selectively adjusting a depth of cut of said milling head.

10. The orthopedic apparatus according to claim 9 wherein said means for securing said spacer comprise a plunger and a plurality of holes in said housing for selectively receiving said plunger.

11. The orthopedic apparatus according to claim 10 wherein said means for receiving torsional forces comprise a drive shaft and wherein said means for turning comprise a rod connected at one end to said U-joint and at a second end to said milling head.

* * * * *